United States Patent
Kim et al.

(10) Patent No.: US 12,083,822 B2
(45) Date of Patent: Sep. 10, 2024

(54) CASTER UNIT AND MEDICAL APPARATUS INCLUDING SAME

(71) Applicant: SAMSUNG MEDISON CO., LTD., Hongcheon-gun Gangwon-do (KR)

(72) Inventors: Yoenho Kim, Seongnam-si (KR); Namyun Kim, Seongnam-si (KR); Wanki Kim, Seongnam-si (KR); Sungtae Sim, Seongnam-si Gyeonggi-do (KR); Junyoung Jung, Seongnam-si Gyeonggi-do (KR); Wonchul Choi, Seongnam-si Gyeonggi-do (KR)

(73) Assignee: SAMSUNG MEDISON CO. LTD., Gangwon-do (KR)

( * ) Notice: Subject to any disclaimer, the term of this patent is extended or adjusted under 35 U.S.C. 154(b) by 711 days.

(21) Appl. No.: 17/267,939

(22) PCT Filed: Nov. 28, 2018

(86) PCT No.: PCT/KR2018/014813
§ 371 (c)(1),
(2) Date: Feb. 11, 2021

(87) PCT Pub. No.: WO2020/036262
PCT Pub. Date: Feb. 20, 2020

(65) Prior Publication Data
US 2021/0213777 A1   Jul. 15, 2021

(30) Foreign Application Priority Data

Aug. 14, 2018  (KR) ........................ 10-2018-0095160

(51) Int. Cl.
| | |
|---|---|
| *B60B 33/00* | (2006.01) |
| *A61B 8/00* | (2006.01) |
| *B62B 3/00* | (2006.01) |

(52) U.S. Cl.
CPC ........ *B60B 33/0015* (2013.01); *A61B 8/4405* (2013.01); *B60B 33/0049* (2013.01);
(Continued)

(58) Field of Classification Search
CPC ............ B60B 33/0015; B60B 33/0049; B60B 33/0057; B60B 33/0068; B60B 33/0042;
(Continued)

(56) References Cited

U.S. PATENT DOCUMENTS 4,318,204 A * 3/1982 Black ....................... F16C 33/61
16/46
6,938,908 B2 9/2005 Oda et al.
(Continued)

FOREIGN PATENT DOCUMENTS

DE    202010010103 U1    12/2011
EP       0075910 A1     4/1983
(Continued)

OTHER PUBLICATIONS

Translation of Sato (JP 2008006190 A) (Year: 2008).*
(Continued)

*Primary Examiner* — James A Shriver, II
*Assistant Examiner* — Nicholas R. Kandas
(74) *Attorney, Agent, or Firm* — Morgan, Lewis & Bockius LLP (57) ABSTRACT

A medical apparatus according to an embodiment of the present invention includes: a medical device; and a plurality of caster units, disposed below the medical device, for supporting the medical device to be movable, wherein each of the plurality of caster units includes: a wheel part; and a shock absorbing member which is configured to support the wheel part and to absorb the shock applied to the wheel part, wherein the shock absorbing member includes: a wheel fixing member for fixing the wheel part; a body fixing (Continued)

member which surrounds the wheel fixing member and is fixed to the medical device; and a cushioning member which is disposed between the wheel fixing member and the body fixing member and is capable of elastic deformation, wherein the shock absorbing member includes: a first deforming part extending in the vertical direction; and a second deformation part extending, from an end of the first deformation part, in a direction different from the extending direction of the first deformation part.

12 Claims, 9 Drawing Sheets

(52) U.S. Cl.
CPC ...... *B60B 33/0057* (2013.01); *B60B 33/0068* (2013.01); *B62B 3/00* (2013.01); *A61B 8/54* (2013.01); *A61B 8/56* (2013.01); *B60B 33/0042* (2013.01); *B60B 33/0073* (2013.01); *B60B 2200/26* (2013.01); *B60B 2900/212* (2013.01); *B62B 2202/00* (2013.01); *B62B 2301/044* (2013.01)

(58) Field of Classification Search
CPC ............ B60B 33/0073; B60B 2200/26; B60B 2900/212; A61B 8/4405; A61B 8/54; A61B 8/56; B62B 3/00; B62B 2202/00; B62B 2301/044
See application file for complete search history.

(56) References Cited

U.S. PATENT DOCUMENTS

| | | | |
|---|---|---|---|
| 7,946,600 B2 | 5/2011 | Kobayashi | |
| 8,152,184 B2 | 4/2012 | Kuttner et al. | |
| 8,365,354 B1 | 2/2013 | Fan | |
| 8,904,598 B2 | 12/2014 | Waitz | |
| 10,226,977 B2 | 3/2019 | Coppuck | |
| 10,292,877 B2 | 5/2019 | Trepanier et al. | |
| 10,471,789 B2 | 11/2019 | Matsushita | |
| 11,351,817 B2 † | 6/2022 | Brischke | |
| 2008/0116660 A1 | 5/2008 | Nicholls | |
| 2013/0097808 A1* | 4/2013 | Long | B60B 33/0023 16/18 CG |
| 2017/0065474 A1 | 3/2017 | Trepanier et al. | |
| 2020/0237585 A1* | 7/2020 | Altinors | F16F 1/127 |
| 2021/0053395 A1* | 2/2021 | Brischke | B60B 33/045 |

FOREIGN PATENT DOCUMENTS

| | | | |
|---|---|---|---|
| EP | 2228240 B1 | | 1/2016 |
| JP | 2000177305 A | * | 6/2000 |
| JP | 2002-347407 A | | 12/2002 |
| JP | 2008006190 A | * | 1/2008 |
| JP | 2013-532097 A | | 8/2013 |
| KR | 10-2012-0041017 A | | 4/2012 |
| KR | 20-0469797 Y1 | | 11/2013 |
| KR | 10-2017-0005050 A | | 1/2017 |
| KR | 10-1859436 B1 | | 5/2018 |
| KR | 10-2020-0108900 A | | 9/2020 |
| WO | 2016/147371 A1 | | 9/2016 |

OTHER PUBLICATIONS

Translation of Watanabe (JP 2000177305 A) (Year: 2000).*
Extended European Search Report dated Sep. 27, 2022 issued in European Patent Application No. 18930093.2.
Korean Office Action dated Jan. 27, 2023 issued in Korean Patent Application No. 10-2018-0095160 (with English translation).
International Written Opinion and Search Report dated May 9, 2019 issued in International Patent Application No. PCT/KR2018/014813 (English translation).
Office Action issued in corresponding European Patent Application No. 18930093.2 dated Jun. 28, 2023.
Office Action issued in corresponding Korean Patent Application No. 10-2018-0095160 dated Apr. 4, 2023, with English translation.
European Notice of Allowance dated Feb. 13, 2024 issued in European Patent Application No. 18930093.2.

* cited by examiner
† cited by third party

CASTER UNIT AND MEDICAL APPARATUS INCLUDING SAME

CROSS-REFERENCE OF RELATED APPLICATIONS

This application is the U.S. National Phase under 35 U.S.C. § 371 of International Patent Application No. PCT/KR2018/014813, filed on Nov. 28, 2018, which in turn claims the benefit of Korean Application No. 10-2018-0095160, filed on Aug. 14, 2018, the entire disclosures of which applications are incorporated by reference herein.

TECHNICAL FIELD

The present invention relates to a caster unit and a medical apparatus including the same.

BACKGROUND ART

A medical apparatus includes medical device and a plurality of caster units arranged below a body of the medical device. A user may freely move the position of the medical apparatus through the plurality of caster units.

However, in a process of moving the position of the medical apparatus, an impact may be applied to the caster units. For example, when the caster units pass over obstacles such as door sills, an impact may be applied to the caster units. In this way, the impact applied to the caster units increases as the weight of the medical device supported by the caster units increases.

In this way, when the impact applied to the caster units is large, the caster units or a part of the medical apparatus including the same may be damaged.

In order to prevent the damage to the caster units or the medical apparatus, various attempts have been made.

As an example, a material of wheels may be changed to a material that is easily elastically deformed. However, in this case, there was a limit to absorbing a large impact.

As another example, the medical apparatus may further include a separate impact absorption part that absorbs impacts between the wheels of the cater units and the medical device. The impact absorption part is classified into a method of absorbing an impact by being deformed in a vertical direction and a method of absorbing an impact by being deformed in a horizontal direction.

The method of absorbing an impact by being deformed in a vertical direction has disadvantages in that a structure is complex, a volume is large, and a design is not classy.

On the other hand, the method of absorbing an impact by being deformed in a horizontal direction is usable in terms of design but has disadvantages in that it is difficult to control the posture of the medical device due to tilting of the medical device due to the load of the medical device, and when an impact is applied, a displacement is large, and thus an impact may not be sufficiently absorbed.

DISCLOSURE

Technical Problem

The present invention is directed to providing a caster unit including an impact absorption part having a relatively simple structure and high impact absorption properties and a medical apparatus including the same. Through high impact absorption, damage due to an external force generated during the distribution or movement of the medical apparatus may be prevented.

In addition, the present invention is directed to providing a caster unit that may suppress or minimize the transmission of uncomfortable vibrations to a user through high impact absorption characteristics, and a medical apparatus including the same.

Technical Solution

One aspect of the present invention provides a medical apparatus according to an embodiment including medical device and a plurality of caster units which are arranged below the medical device and movably support the medical device, wherein each of the plurality of caster units includes a wheel part that includes a wheel, a wheel support part supporting the wheel to be rotatable with reference to a first rotational axis parallel to a ground, and a caster support part connected to a portion of the wheel support part that is spaced apart from the first rotational axis and extending in a direction perpendicular to the first rotational axis: and an impact absorption part configured to support the wheel part and absorb an impact applied to the wheel part, the impact absorption part includes: a wheel fixing member surrounding the caster support part and fixed to the caster support part: a body fixing member surrounding the wheel fixing member and fixed to the medical device; and a buffer member that is disposed between the wheel fixing member and the body fixing member and elastically deformable, and the buffer member includes: a first deformation part extending in a direction parallel to an extension direction of the caster support part: and a second deformation part extending from the first deformation part in a direction different from a extension direction of the first deformation part.

The cross-sectional shape of the buffer member may have an L shape.

The cross-sectional shape of the wheel fixing member may have an L shape.

The first deformation part has a first groove disposed in one end thereof.

The first deformation part may include a first contact portion in contact with the wheel fixing member and a second contact portion in contact with the body fixing member, and an end of the first contact portion may be disposed lower than an end of the wheel fixing member.

The second deformation part may have a second groove disposed in one end thereof.

An end of the wheel fixing member may be spaced apart from the body fixing member in an extension direction of the caster support part such that a space is formed between the wheel fixing member and the body fixing member.

A liquid may fill the space.

The Shore A hardness of the buffer member may be in the range of 40 to 80.

The thickness of the first deformation part may be different from the thickness of the second deformation part.

The length of the first deformation part may be different from the length of the second deformation part.

A connection portion between the first deformation part and the second deformation part may have a curved shape.

The maximum diameter of the buffer member may be smaller than two times a distance from the first rotational axis to a central line of the caster support part.

The weight of the medical device may be in the range of 30 kg to 200 kg.

The body fixing member may include a fixing part fixed to the medical device and a bush part that is detachably attached to the fixing part and faces the buffer member.

Another aspect of the present invention provides a caster unit which includes the caster unit described above and is disposed below medical device and movably support the medical device.

Advantageous Effects

A caster unit and a medical apparatus including the same according to embodiments can have a relatively simple structure and sufficient impact absorption characteristics by improving a structure of an impact absorption part.

In addition, in the caster unit and the medical apparatus including the same according to the embodiments, the transmission of uncomfortable vibrations to a user can be suppressed or minimized through high impact absorption characteristics and damage due to an external force generated during the distribution or movement can be prevented.

MODES OF THE INVENTION

The present specification describes the principles of the present invention and discloses embodiments such that the scope of the present invention is clarified and those skilled in the art to which the present invention pertains implement the present invention. The disclosed embodiments may be implemented in various forms.

Throughout the specification, the same reference numerals refer to the same components. The present specification does not describe all components of the embodiments, and general contents or duplicated contents between the embodiments in the technical field to which the present invention pertains will be omitted. Terms such as "part" or "portion" used in the specification may be implemented with software or hardware, and according to the embodiments, a plurality of "parts" or "portions" may be implemented as one unit or element and one "part" or "portion" may include a plurality of units or elements. Hereinafter, the operating principles and embodiments of the present invention will be described with reference to the accompanying drawings.

Hereinafter, the embodiments will be described in detail with reference to the accompanying drawings.

Figure 1:
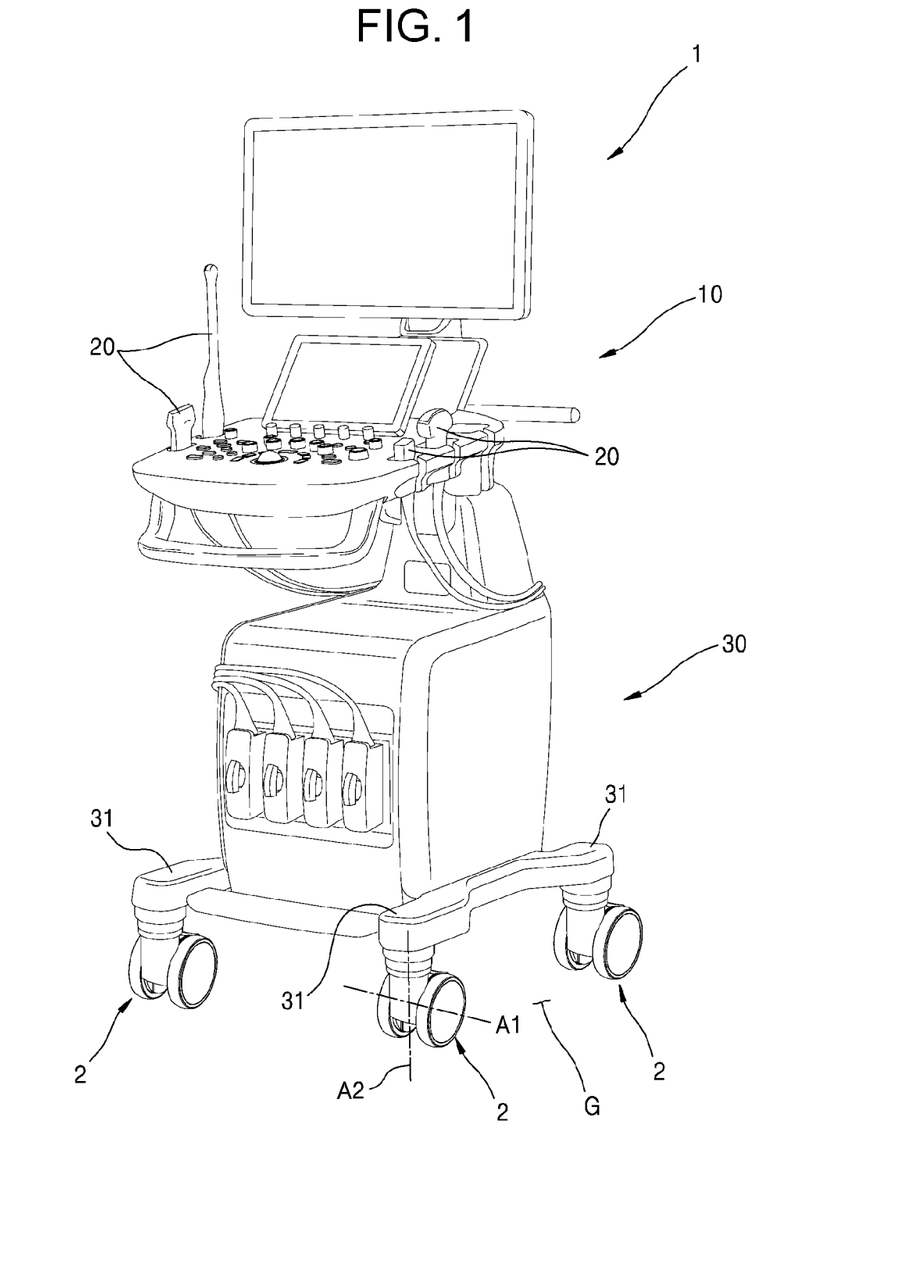
FIG. 1 is a perspective view illustrating a medical apparatus according to an embodiment.
Figure 2:
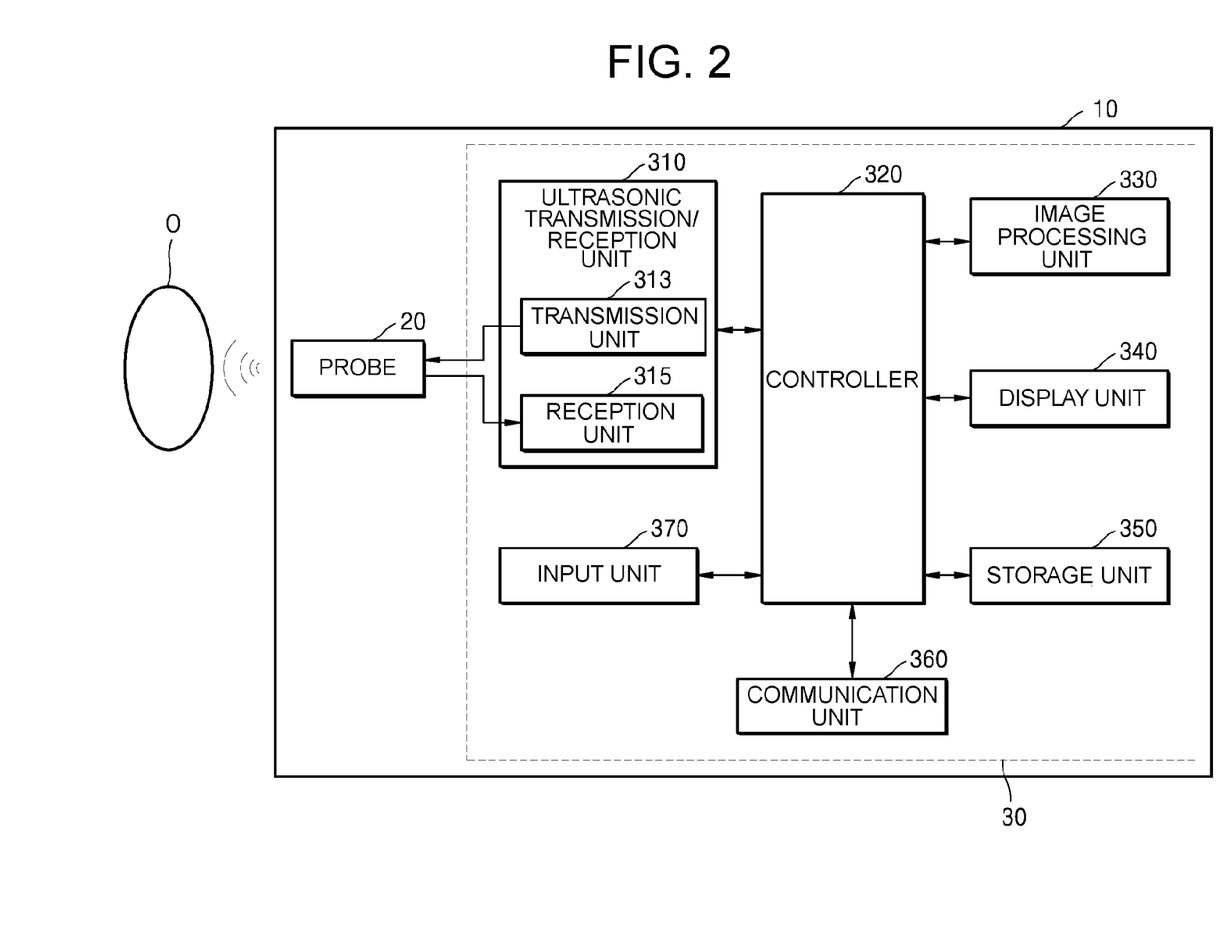
FIG. 2 is a block diagram illustrating a configuration of medical device according to the embodiment.
Figure 3:
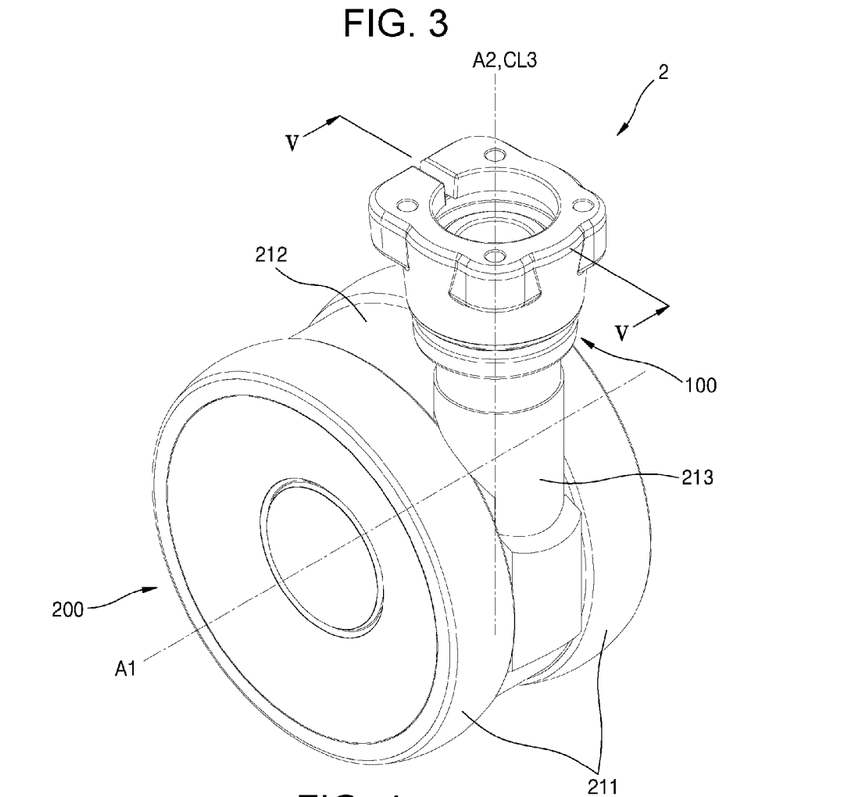
FIG. 3 is a perspective view illustrating a caster unit according to the embodiment.

FIG. 1 is a perspective view illustrating a medical apparatus according to an embodiment. FIG. 2 is a block diagram illustrating a configuration of medical device according to the embodiment. FIG. 3 is a perspective view illustrating a caster unit according to the embodiment.

Referring to FIG. 1, a medical apparatus 1 according to the embodiment includes medical device 10 and a plurality of caster units 2 movably supporting the medical device 10.

Referring to FIGS. 1 and 2, as an example, the medical device 10 may be ultrasonic equipment. The medical device 10 includes a probe 20 and a body 30.

The body may include an ultrasonic transmission/reception unit 310, a controller 320, an image processing unit 330, a display unit 340, a storage unit 350, a communication unit 360, and an input unit 170.

The probe 20 may include a plurality of transducers. The plurality of transducers may transmit ultrasonic signals to an object O according to a transmission signal applied from a transmission unit 313. The plurality of transducers may receive ultrasonic signals reflected from the object O to form a reception signal.

The medical device 10 may include one or more probes 20 according to an implementation form.

The controller 320 controls the transmission unit 313 to form a transmission signal to be applied to each of the plurality of transducers in consideration of locations and focal points of the plurality of transducers included in the probe 20.

The controller 320 controls a reception unit 315 to convert a reception signal received from the probe 20 using an analog-to-digital conversion method and to sum the digitally converted reception signal in consideration of the positions and focal points of the plurality of transducers, thereby generating ultrasonic data.

The image processing unit 330 generates an ultrasonic image using the ultrasonic data generated by the ultrasonic reception unit 315.

The display unit 340 may display the generated ultrasonic image and various pieces of information processed by the medical device 10. The medical device 10 may include one or more display units 340 according to an implementation form. Further, the display unit 340 may be implemented as a touch screen in combination with a touch panel.

The controller 320 may control the overall operation of the medical device 10 and a signal flow between internal components of the medical device 10. The controller 320 may include a memory that stores a program or data for performing a function of the medical device 10 and a processor that processes the program or data. Further, the controller 320 may control the operation of an ultrasonic diagnosis device 10 by receiving a control signal from the input unit 170 or an external device.

The medical device 10 may include the communication unit 360 and may be connected, through the communication unit 360, to an external device (for example, a server, a medical device, a portable device (a smart phone, a tablet PC, a wearable device, or the like)).

The communication unit 360 may include one or more components which may communicate with the external device and may include, for example, at least one of a short-range communication module, a wired communication module, and a wireless communication module.

The communication unit 360 may receive a control signal and data from the external device and transmit the received control signal to the controller 320 so that the controller 320 controls the medical device 10 according the received control signal.

Alternatively, the controller 320 may control the external device according to a control signal of the controller by transmitting the control signal to the external device through the communication unit 360.

For example, the external device may process data of the external device according to the control signal of the controller received through the communication unit.

A program that may control the medical device 10 may be installed in the external device, and the program includes a command for performing some or all of the operations of the controller 320.

The program may be installed in advance in the external device, or a user of the external device may download and install a program from a server providing an application in the external device. The server providing an application may include a recording medium in which the corresponding program is stored.

The storage unit 350 may store various types of data or programs for driving and controlling the medical device 10, input/output ultrasonic data, acquired ultrasonic images, and the like.

The input unit 370 may receive a user's input for controlling the medical device 10. Although the user's input may include, for example, input obtained by manipulating a button, a keypad, a mouse, a trackball, a jog switch, a knob, and the like, input obtained by touching a touch panel or a touch screen, voice input, motion input, biometric information input (for example, iris recognition, fingerprint recognition, and the like), and the like, the present invention is not limited thereto.

Referring back to FIGS. 1 and 3, each of the plurality of caster units 2 is disposed below the medical device 10 and includes a wheel part 200 that is rotatable with respect to the ground G.

The wheel part 200 includes a wheel 211 that rotates while in contact with the ground G, a wheel support part 212 that supports the wheel 211 to be rotatable about a first rotational axis A1 parallel to the ground G, and a caster support part 213 that is connected to a portion of the wheel support part 212 that is spaced apart from the first rotational axis A1.

The caster support part 213 extends in a direction perpendicular to the first rotational axis A1. The caster support part 213 may extend in a direction perpendicular to the ground G. An extension direction of the caster support part 213 may coincide with an extension direction of a second rotational axis A2.

In the wheel part 200, the wheel 211 may rotate about the first rotational axis A1 and the wheel support part 212 rotates about the second rotational axis A2. As the wheel support part 212 rotates about the second rotational axis A2, the direction of the wheel part 200 of the caster unit 2 may be freely changed.

Figure 4:
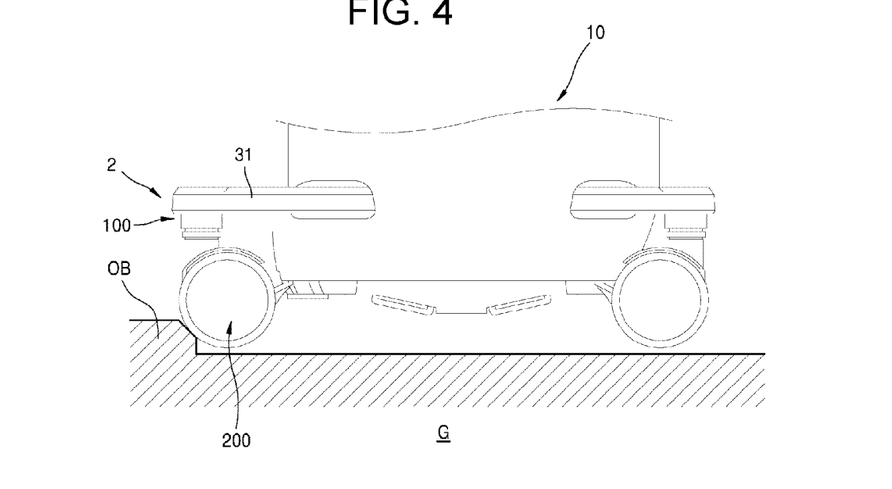
FIG. 4 is a view for describing a process in which the medical apparatus passes over an obstacle according to the embodiment.

FIG. 4 is a view for describing a process in which the medical apparatus 1 passes over an obstacle OB according to the embodiment. Referring to FIGS. 1 and 4, while the caster unit 2 collides with the obstacle OB protruding from the ground G like a door sill, an impact may be applied to the caster unit 2.

The impact applied to the caster unit 2 depends on the weight of the medical device 10 supported by the caster unit 2. For example, the weight of the medical device 10 may be in the range of 30 kg to 200 kg. Even though the weight of the medical device 10 is 30 kg or more, when the caster unit 2 does not include a separate impact absorption part 100, the impact applied to the caster unit 2 may be increased enough to damage a part of the caster unit 2 or the medical device 10.

The caster unit 2 according to the embodiment may further include the impact absorption part 100 configured to absorb an impact applied to the wheel part 200 in consideration of the impact applied to the caster unit 2 supporting the medical device 10. The impact absorption part 100 is disposed between the wheel part 200 and the medical device 10 and supports the wheel part 200.

Figure 5:
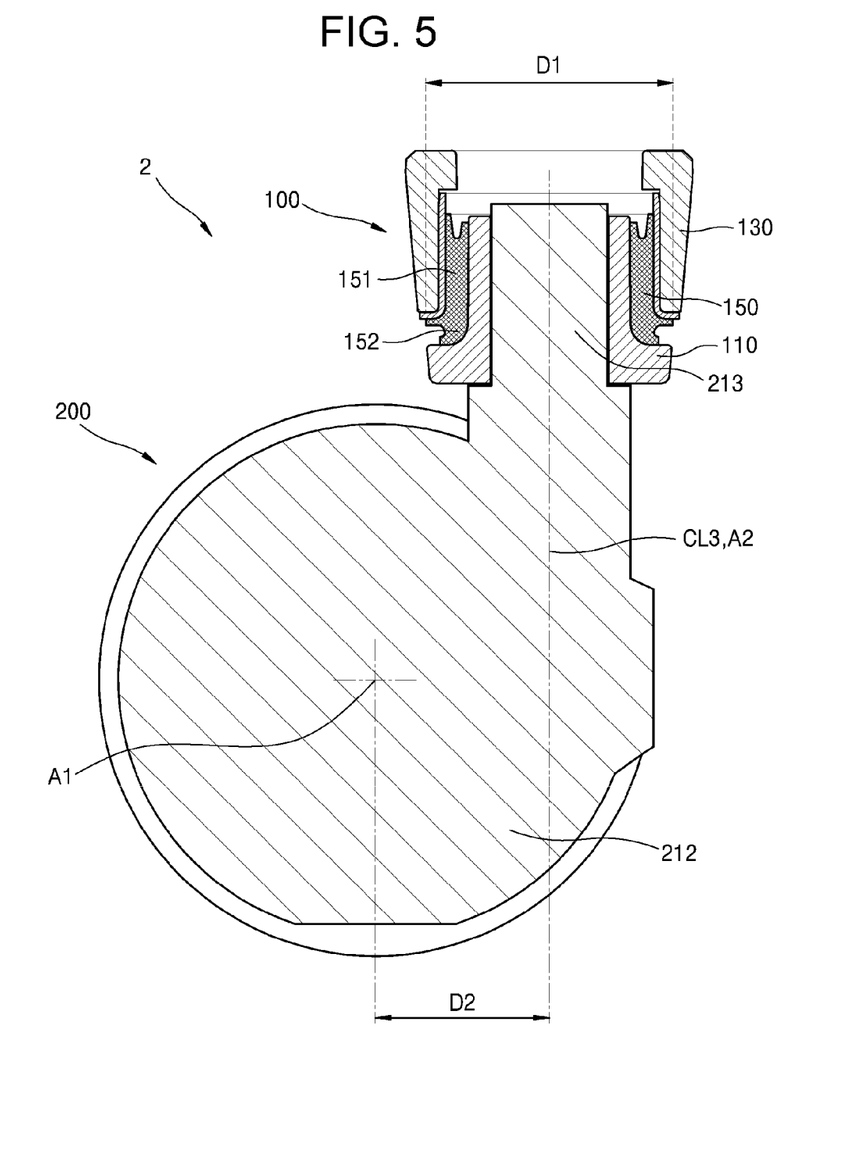
FIG. 5 is a sectional view of the caster unit according to the embodiment.

FIG. 5 is a sectional view of the caster unit 2 according to the embodiment. Referring to FIGS. 3 to 5, the impact absorption part 100 includes a wheel fixing member 110 that surrounds the caster support part 213, a body fixing member 130 that surrounds the wheel fixing member 110, and a buffer member 150 that is disposed between the wheel fixing member 110 and the body fixing member 130.

The wheel fixing member 110 is fixed to the caster support part 213. The wheel fixing member 110 has a predetermined strength or more to fixedly support the caster support part 213. A material of the wheel fixing member 110 may include a metal or non-metal.

The wheel fixing member 110 may have a structure through which the caster support part 213 passes and may be fixed to the caster support part 213 through screw-coupling. For example, the inner peripheral surface of the wheel fixing member 110 and the outer peripheral surface of the caster support part 213 may be screw-coupled to each other. However, fixing between the wheel fixing member 110 and the caster support part 213 is not limited thereto and may be achieved in various manners. For example, although not illustrated, the wheel fixing member 110 may have a flat plate shape through which the caster support part 213 does not pass, and an end of the caster support part 213 and the wheel fixing member 110 may be fixed to each other through a separate fixing member.

The wheel fixing member 110 may be fixed to the caster support part 213 to facilitate separation and assembly. Through this, the wheel fixing member 110 may be assembled and fixed to the wheel part 200 of the caster unit 2 that does not adopt the existing impact absorption part 100.

In the above-described embodiment, a structure in which the wheel fixing member 110 surrounds the caster support part 213 is illustrated, but the present invention is not limited thereto, and the structure may be variously modified as long as the structure is fixed to the caster support part 213.

The body fixing member 130 is fixed to the medical device 10. For example, the body fixing member 130 may be fixed to a wing 31 protruding from a body of the medical device 10. The body fixing member 130 may have a predetermined strength or more to be fixedly supported by the medical device. A material of the body fixing member 130 may include a metal or non-metal. The materials of the body fixing member 130 and the wheel fixing member 110 may be the same in consideration of mass production.

In the above-described embodiment, a structure in which the body fixing member 130 surrounds the wheel fixing member 110 is illustrated, but the present invention is not limited thereto, and the structure may be variously modified.

The buffer member 150 includes a material that may be elastically deformed. As an example, the material of the buffer member 150 may include rubber.

Figure 6:
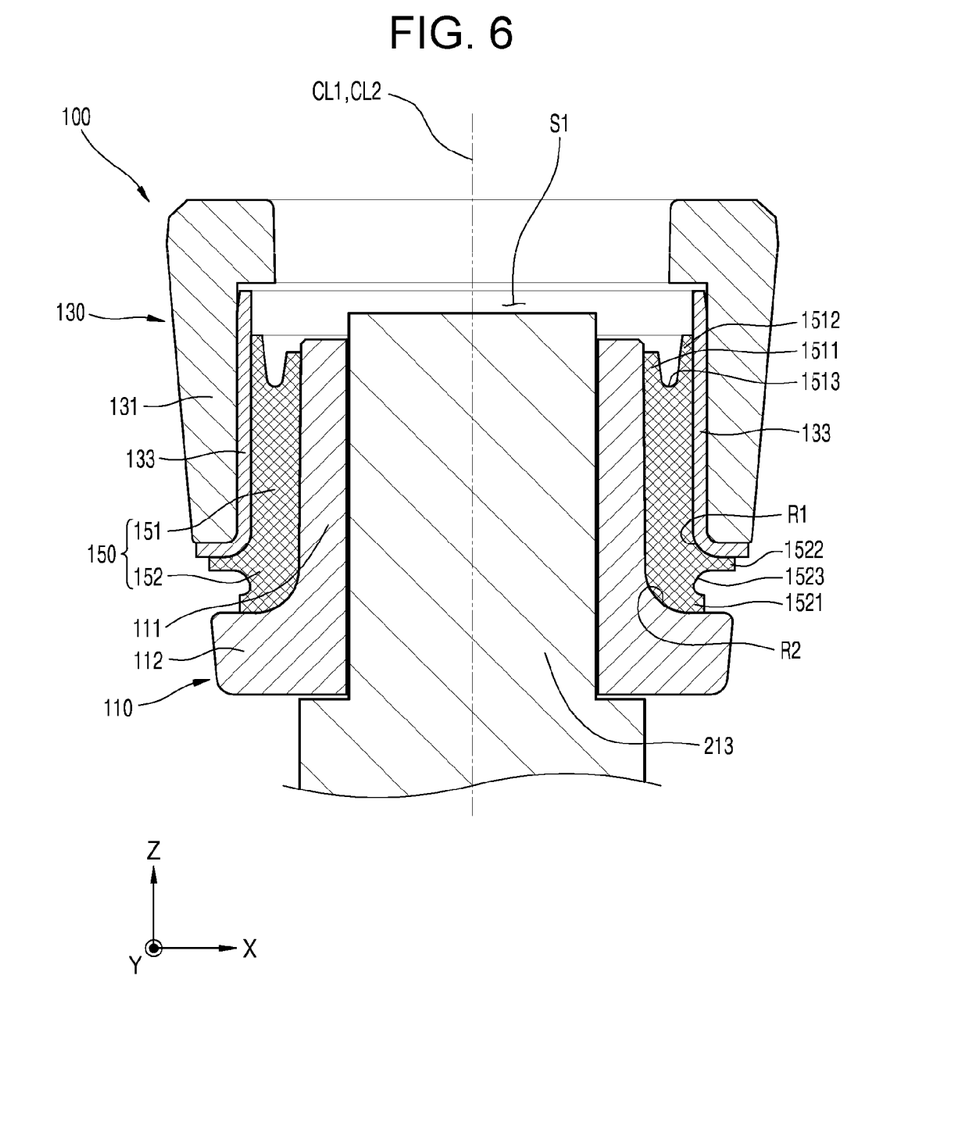
FIG. 6 is an enlarged view illustrating an impact absorption part of FIG. 5.
Figure 7:
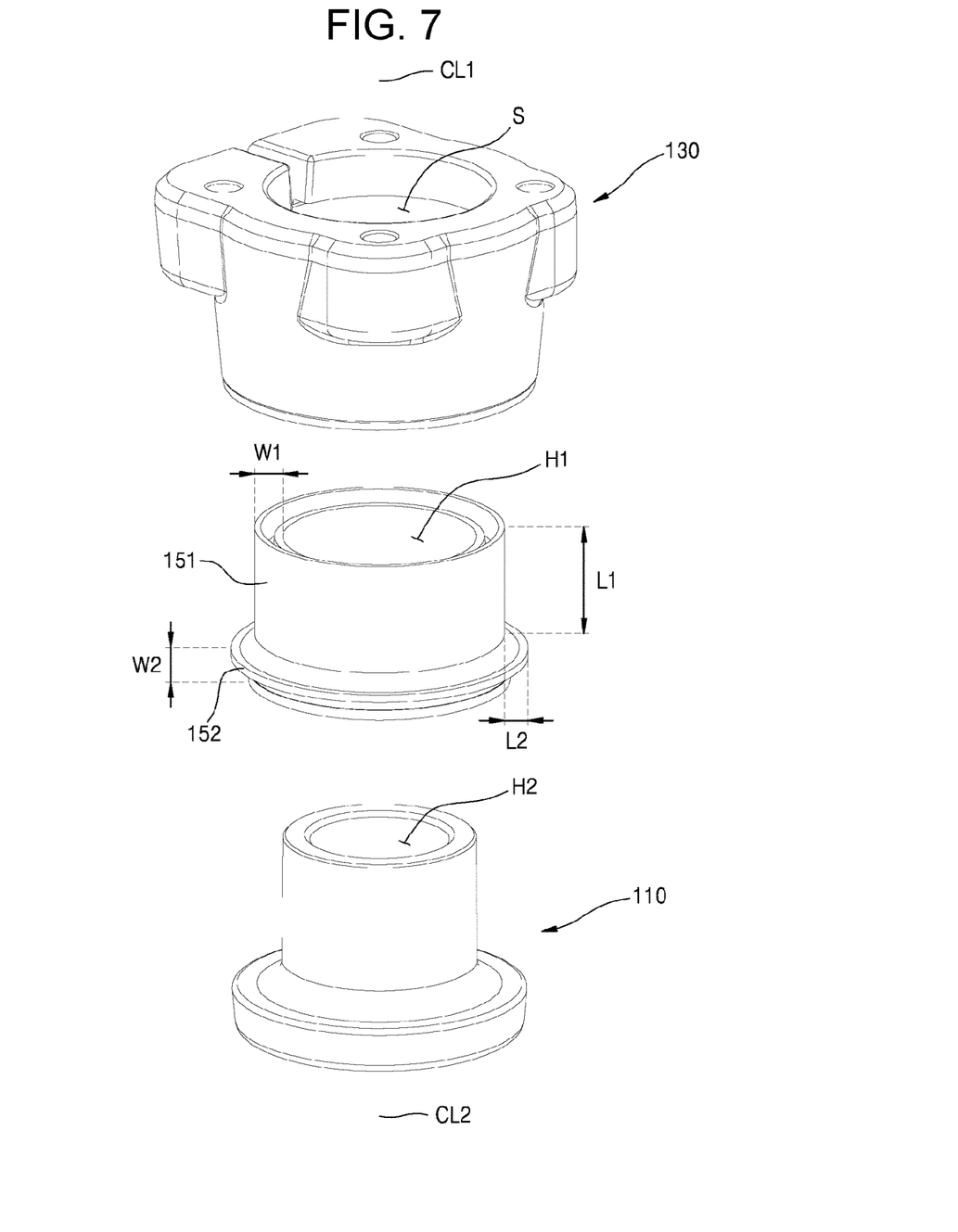
FIG. 7 is an exploded perspective view of the impact absorption part of FIG. 5.

FIG. 6 is an enlarged view illustrating the impact absorption part 100 of FIG. 5. FIG. 7 is an exploded perspective view of the impact absorption part 100 of FIG. 5.

Referring to FIGS. 5, 6, and 7, the impact absorption part 100 according to the embodiment includes the body fixing member 130, the buffer member 150, and the wheel fixing member 110.

Figure 8:
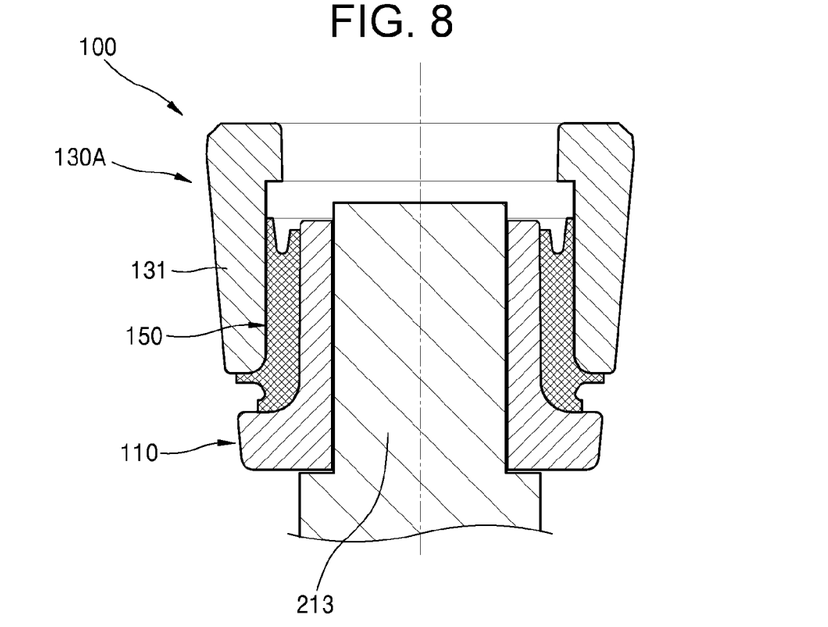
FIG. 8 is an enlarged view illustrating an impact absorption part according to another embodiment.

The body fixing member 130 includes a fixing part 131 fixed to the medical device 10 and a bush part 133 that is detachably attached to the fixing part 131 and faces the buffer member 150. When the weight of the medical device 10, the type of the wheel fixing member 110, or the like is changed, various combinations of the caster unit 2 and the medical device 10 may be achieved by replacing the bush part 133. However, since the bush part 133 of the body fixing member 130 is an optional component, the bush part 133 may be omitted in a body fixing member 130A as shown in FIG. 8.

The body fixing member 130 includes an insertion space S into which a part of the buffer member 150 is inserted. The insertion space S is illustrated as an example having a shape of a through-hole, but is not limited thereto, and may have a groove shape.

The buffer member 150 includes a first through-hole H1 into which a part of the wheel fixing member 110 may be inserted. The wheel fixing member 110 includes a second through-hole H2 into which a part of the caster support part 213 may be inserted.

The buffer member 150 includes a first deformation part 151 extending in a direction parallel to the extension direction of the caster support part 213 and a second deformation part 152 extending from an end of the first deformation part 151 in a direction different from the extension direction of the first deformation part 151.

The cross-sectional shape of the buffer member 150 may include an L shape. As an example, the first deformation part 151 may extend in a direction (Z direction) perpendicular to the ground G, and the second deformation part 152 may extend in a direction (X direction or Y direction) parallel to the ground G.

The cross-sectional shape of the wheel fixing member 110 may include an L shape. As an example, the wheel fixing member 110 includes a vertical part 111 extending in a direction (Z direction) perpendicular to the ground G and a horizontal part extending in a direction (X direction or Y direction) parallel to the ground G.

At least a part of the first deformation part 151 is disposed between the body fixing member 130 and the vertical part 111, and at least a part of the second deformation part 152 is disposed between the body fixing member 130 and the horizontal part 112.

A connection portion between the first deformation part 151 and the second deformation part 152 may have curved shapes R1 and R2. A surface, which faces the buffer member 150, of a connection portion between the vertical part 111 and the horizontal part 112 may have a curved shape R2. A surface of the body fixing member 130 facing the connection portion between the first deformation part 151 and the second deformation part 152 may have a curved shape R1. Through this, the buffer member 150 may be prevented from being damaged during an elastic deformation process.

The buffer member 150 may have grooves formed at both ends thereof. For example, the first deformation part 151 may have a first groove 1513 disposed in one end thereof, and the second deformation part 152 may have a second groove 1523 disposed in one end thereof. The first groove 1513 and the second groove 1523 are formed in both ends of the buffer member 150, and thus natural elastic deformation of the buffer member 150 may be induced.

The first deformation part 151 includes a first contact portion 1511 in contact with the wheel fixing member 110 and a second contact portion 1512 in contact with the body fixing member 130. The first groove 1513 is disposed between the first contact portion 1511 and the second contact portion 1512.

An end of the first contact portion 1511 may be disposed lower than an end of the wheel fixing member 110. The end of the first contact portion 1511 may be disposed lower than an end of the caster support part 213. Accordingly, while the caster support part 213 and the wheel fixing member 110 fixed to the caster support part 213 are tilted, the first contact portion 1511 may be prevented from coming into contact with the end of the caster support part 213 or the end of the wheel fixing member 110. Thus, damage to the first contact portion 1511 may be prevented.

Ends of the wheel fixing member 110 may be spaced apart from each other in the extension direction of the caster support part 213 from the body fixing member 130. Ends of the wheel fixing member 110 may be spaced apart from each other in the extension direction of the caster support part 213 from the caster support part 213. Accordingly, a predetermined space S1 may be formed between the wheel fixing member 110 and the body fixing member 130.

Through the space S1, when an impact is applied to the caster unit 2, the caster support part 213 and the wheel fixing member 110 fixed to the caster support part 213 may not collide with the body fixing member 130 and may be tilted.

In the first deformation part 151, an end of the second contact portion 1512 may be disposed higher than the end of the first contact portion 1511 in a vertical direction. The end of the second contact portion 1512 may be disposed higher than the end of the wheel fixing member 110 in the vertical direction.

A predetermined fluid may fill the space S1. As an example, gas such as air may fill the space S1. As another example, a liquid may fill the space.

The second deformation part 152 includes a third contact portion 1521 in contact with the wheel fixing member 110 and a fourth contact portion 1522 in contact with the body fixing member 130. The second groove 1523 is disposed between the third contact portion 1521 and the fourth contact portion 1522. The fourth contact portion 1522 may protrude from the third contact portion 1521.

The buffer member 150 may have a predetermined hardness. For example, the buffer member 150 may have a Shore A hardness of 40 to 80.

In the buffer member 150, a length L1 of the first deformation part 151 may be different from a length L2 of the second deformation part 152. For example, the length L1 of the first deformation part 151 in the vertical direction may be larger than the length L2 of the second deformation part 152 in the horizontal direction.

In the buffer member 150, a thickness W1 of the first deformation part 151 may be different from a thickness W2 of the second deformation part 152. For example, the thickness W1 of the first deformation part 151 in the horizontal direction may be smaller than the thickness W2 of the second deformation part 152 in the vertical direction. However, the thickness W1 of the first deformation part 51 and the thickness W2 of the second deformation part 152 are not limited thereto and, of course, may be the same.

By designing the shape and hardness of the buffer member 150 as described above, an angle between a central line CL1 of the body fixing member 130 and a central line CL2 of the wheel fixing member 110 may be maintained at a predetermined angle or less. For example, in the buffer member 150, even when an external impact is applied to the caster unit 2, the angle between the central line CL1 of the body fixing member 130 and the central line CL2 of the wheel fixing member 110 may be maintained at 3 degrees or less. Since the wheel fixing member 110 is in a state of being fixed to the caster support part 213, the central line CL2 of the wheel fixing member 110 coincides with a central line CL3 of the caster support part 213.

Referring back to FIG. 5, a maximum diameter D1 of the buffer member 150 may be smaller than two times a distance D2 from the first rotational axis A1 to the central line CL3 of the caster support part 213. Here, the maximum diameter D1 of the buffer member 150 may be a maximum diameter of the second deformation part 152. The central line CL3 of the caster support part 213 may coincide with the rotational axis A2 of the caster support part 213.

At least a part of the buffer member 150 may be disposed to overlap the wheel part 200. For example, an area of the buffer member 150, which overlaps the wheel part 200 in the vertical direction, may be 70% or more of the total area of the buffer member 150.

By designing the impact absorption part 100 as described above, a structure is relatively simple, a design is good, posture control of the medical device 10 is easy, and predetermined impact absorption characteristics may be secured.

Figure 10:
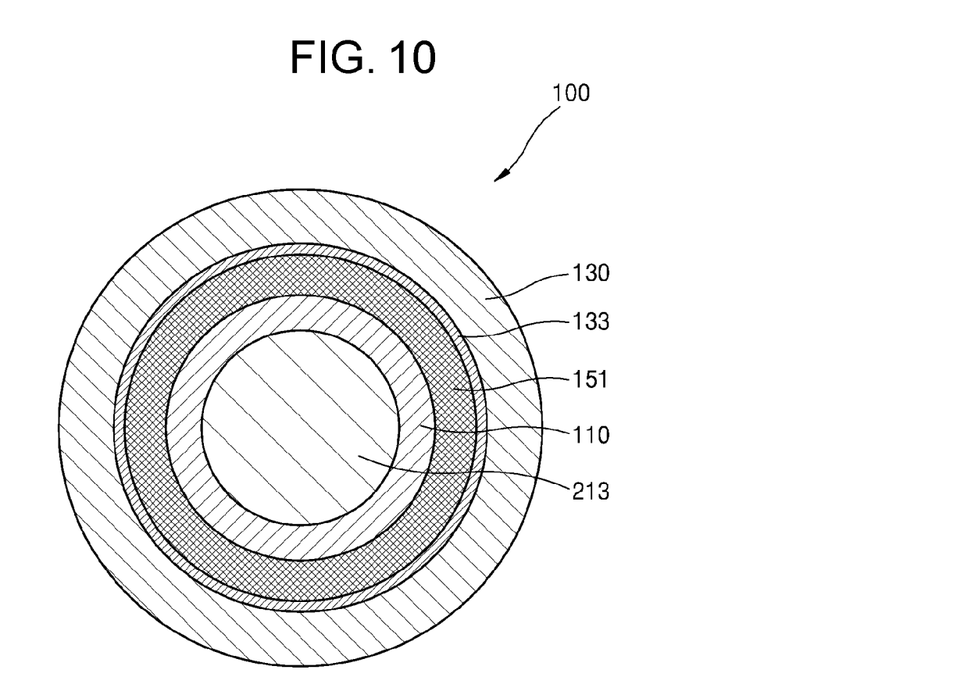
FIG. 10 is a sectional view of the impact absorption part of FIG. 5, which is cut in a horizontal direction.
Figure 11A:
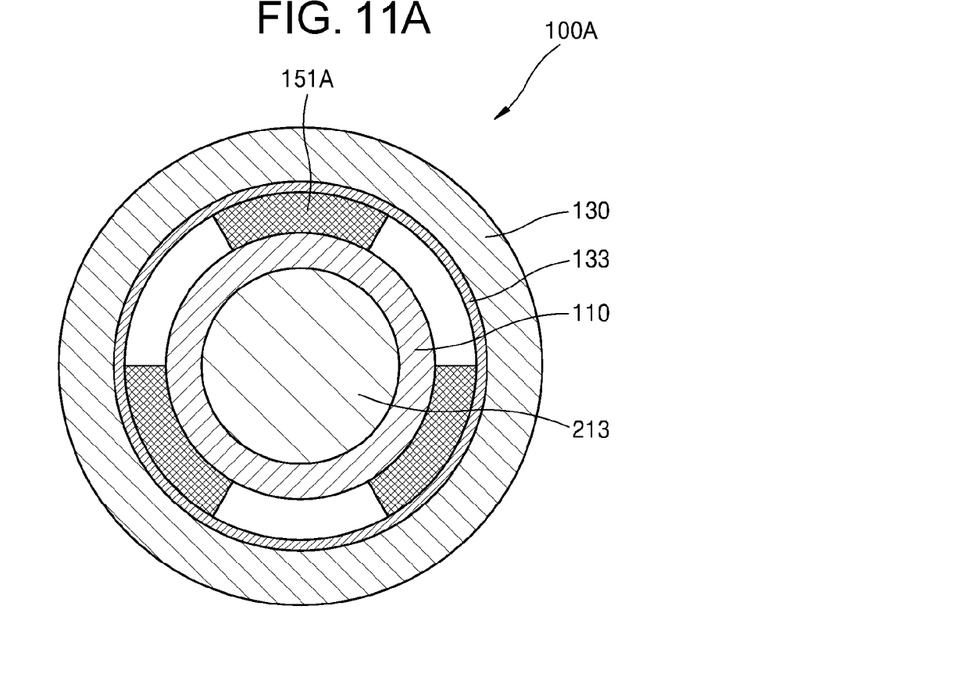
FIGS. 11A and 11B are sectional views of an impact absorption part according to another embodiment, which is cut in the horizontal direction.
Figure 11B:
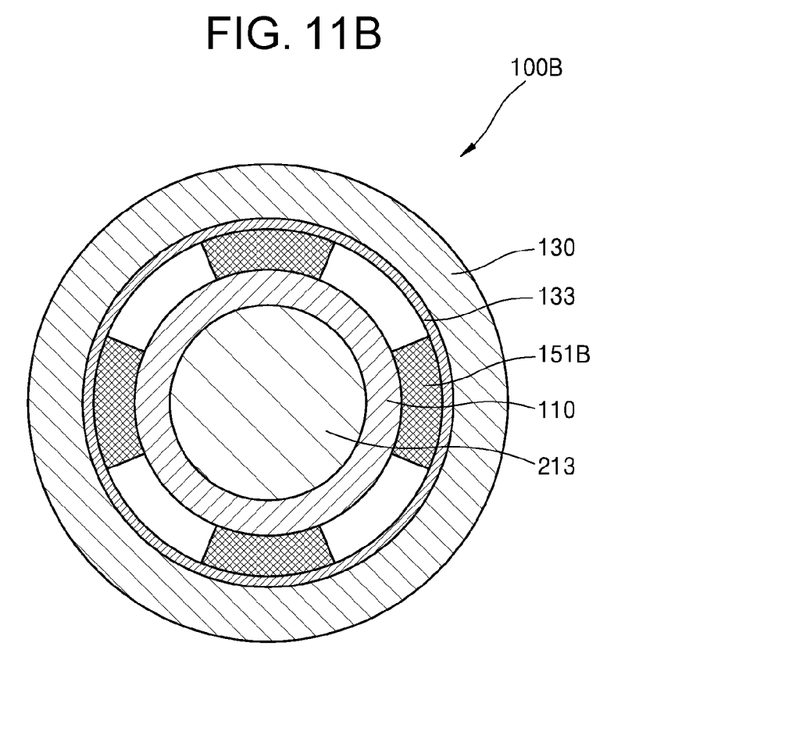

FIG. 10 is a sectional view of the impact absorption part 100 of FIG. 5, which is cut in a horizontal direction, and FIGS. 11A and 11B are sectional views of impact absorption parts 100A and 100B according to another embodiment, which is cut in the horizontal direction.

In the above-described embodiment, as illustrated in FIG. 10, the description has been made mainly on an example where the buffer member 150 is entirely disposed between the wheel fixing member 110 and the body fixing member 130, but the present invention is not limited thereto. For example, referring to FIGS. 11A and 11B, buffer members 150A and 150B of the impact absorption parts 100A and 100B may be partially disposed between the wheel fixing member 110 and the body fixing member 130.

Next, the operation of the impact absorption part 100 according to the embodiment will be described.

Figure 9:
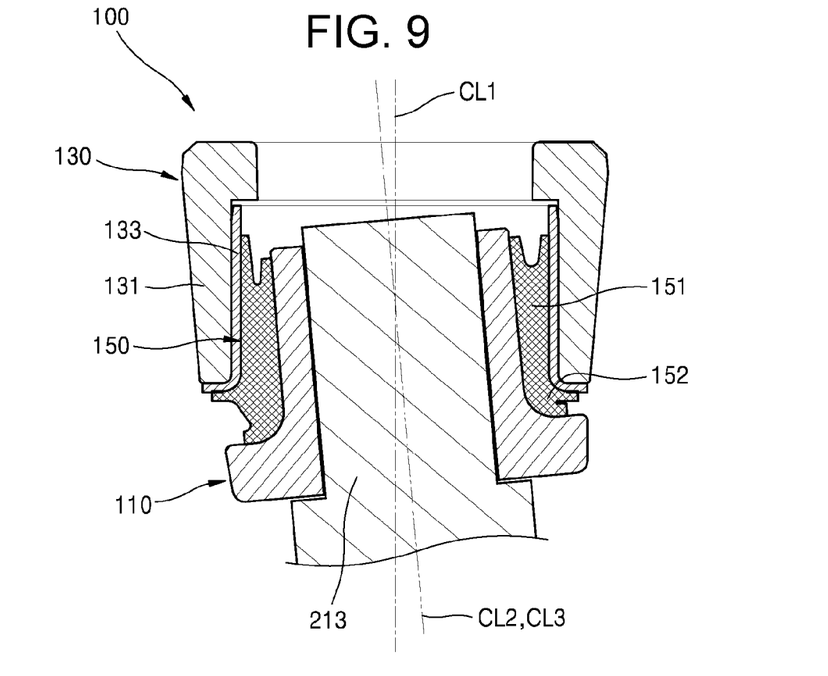
FIG. 9 is a view illustrating the operation of the impact absorption part when the caster unit passes over an obstacle.

FIG. 9 is a view illustrating the operation of the impact absorption part 100 when the caster unit 2 passes over the obstacle. Referring to FIGS. 4 and 9, as the caster unit 2 moves in a direction approaching the obstacle OB, the wheel part 200 of the caster unit 2 collides with the obstacle OB. While the wheel part 200 collides with the obstacle OB, an impact acts on the wheel part 200, and accordingly, the caster support part 213 of the wheel part 200 and the wheel fixing member 110 fixed to the caster support part 213 are tilted with respect to the body fixing member 130. For example, before the caster unit 2 collides with the obstacle OB, the central line CL2 of the wheel fixing member 110 and the central line CL1 of the body fixing member 130 coincide with each other as illustrated in FIG. 6, and while the caster unit 2 collides with the obstacle OB, the central line CL2 of the wheel fixing member 110 and the central line CL1 of the body fixing member 130 are misaligned with each other as illustrated in FIG. 9.

While the wheel part 200 and the wheel fixing member 110 are tilted, the first deformation part 151 of the buffer member 150 is elastically deformed in a horizontal direction and primarily absorbs the impact. While the wheel part 200 and the wheel fixing member 110 are tilted, the second deformation part 152 of the buffer member 150 is elastically deformed in a vertical direction, secondarily absorbs the impact, and limits tilt angles of the wheel part 200 and the wheel fixing member 110. While being elastically deformed in the vertical direction, the second deformation part 152 limits the tilt angles of the wheel part 200 and the wheel fixing member 110 and, at the same time, absorbs the impact in the vertical direction.

When the buffer member 150 includes only the first deformation part 151 without the second deformation part 152, it is difficult to control the tilt angle of the wheel part 200 while the impact is absorbed. For example, by increasing the thickness of the first deformation part 151 in the buffer member 150, the impact applied to the caster unit 2 may be absorbed, but it is difficult to satisfy control of the tilt angle of the wheel part 200.

On the other hand, since the buffer member 150 according to the embodiment includes the first deformation part 151 and the second deformation part 152, an impact can be absorbed, and at the same time, the tilt angle of the wheel part 200 can be controlled.

Those skilled in the technical field related to the embodiments of the present invention will understand that the present invention may be implemented in a modified form without departing from the essential feature of the description. Therefore, the disclosed methods should be considered not from a limitative viewpoint not an explanatory viewpoint. The scope of the present invention is disclosed but in the detailed description of the invention but in the appended claims, and all differences within the scope equivalent thereto should be construed as being included in the scope of the present invention.

The invention claimed is:

1. A medical apparatus comprising a medical device and a plurality of caster units which are arranged below the medical device and movably support the medical device, wherein each of the plurality of caster units includes:
   a wheel part that includes a wheel, a wheel support part supporting the wheel to be rotatable with reference to a first rotational axis parallel to a ground, and a caster support part connected to a portion of the wheel support part that is spaced apart from the first rotational axis and extending in a direction perpendicular to the first rotational axis; and
   an impact absorption part configured to support the wheel part and absorb an impact applied to the wheel part,
   the impact absorption part includes:
      a wheel fixing member surrounding the caster support part and fixed to the caster support part;
      a body fixing member surrounding the wheel fixing member and fixed to the medical device; and
      a buffer member that is disposed between the wheel fixing member and the body fixing member and elastically deformable, and
   the buffer member includes:
      a first deformation part extending in a direction parallel to an extension direction of the caster support part; and
      a second deformation part extending from the first deformation part in a direction different from an extension direction of the first deformation part,
   wherein the first deformation part has a first groove disposed in one end thereof,
   the second deformation part has a second groove disposed in another end thereof,
   a thickness of the first deformation part in the direction different from the extension direction of the first deformation part is smaller than a thickness of the second deformation part in the extension direction of the caster support part, and the first groove and the second groove are comprised to allow natural elastic deformation of the buffer member.

2. The medical apparatus of claim 1, wherein a cross-sectional shape of the buffer member has an L shape.

3. The medical apparatus of claim 2, wherein a cross-sectional shape of the wheel fixing member has an L shape.

4. The medical apparatus of claim 1, wherein:
the first deformation part includes a first contact portion in contact with the wheel fixing member and a second contact portion in contact with the body fixing member; and
an end of the first contact portion is disposed lower than an end of the wheel fixing member.

5. The medical apparatus of claim 1, wherein an end of the wheel fixing member is spaced apart from the body fixing member in the extension direction of the caster support part such that a space is formed between the wheel fixing member and the body fixing member.

6. The medical apparatus of claim 1, wherein a Shore A hardness of the buffer member is in a range of 40 to 80.

7. The medical apparatus of claim 1, wherein a length of the first deformation part is different from a length of the second deformation part.

8. The medical apparatus of claim 1, wherein a connection portion between the first deformation part and the second deformation part has a curved shape.

9. The medical apparatus of claim 1, wherein a maximum diameter of the buffer member is smaller than two times a distance from the first rotational axis to a central line of the caster support part.

10. The medical apparatus of claim 1, wherein a weight of the medical device is in a range of 30 kg to 200 kg.

11. The medical apparatus of claim 1, wherein the body fixing member includes a fixing part fixed to the medical device and a bush part that is detachably attached to the fixing part and faces the buffer member.

12. A caster unit which includes the plurality of caster units according to claim 1 and is disposed below medical device and movably supports the medical device.

* * * * *